United States Patent [19]

Georgiev et al.

[11] Patent Number: 4,835,283
[45] Date of Patent: May 30, 1989

[54] 3,5-DIPHENYL-3-[(1H-IMIDAZOL-1-YLMETHYL) OR (1H-1,2,4-TRIAZOL-1-YLMETHYL)]-2-METHYL-4-ISOXAZOLINES

[75] Inventors: Vassil S. Georgiev, Penfield; George B. Mullen, Avon, both of N.Y.

[73] Assignee: Pennwalt Corporation, Philadelphia, Pa.

[21] Appl. No.: 167,673

[22] Filed: Mar. 7, 1988

[51] Int. Cl.$^4$ .................... A61K 31/41; C07D 261/04
[52] U.S. Cl. .................... 548/240; 548/265; 548/341
[58] Field of Search .................... 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1976 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | St. Georgiev et al. | 548/240 |
| 4,723,021 | 2/1988 | St. Georgiev et al. | 548/240 |
| 4,727,156 | 2/1988 | St. Georgiev et al. | 548/240 |
| 4,727,157 | 2/1988 | St. Georgiev et al. | 548/240 |
| 4,769,471 | 9/1988 | Georgiev | 548/240 |

FOREIGN PATENT DOCUMENTS

| | | | |
|---|---|---|---|
| 171137 | 2/1986 | European Pat. Off. | 548/215 |
| 54-76579 | 6/1979 | Japan . | |
| 1288213 | 9/1972 | United Kingdom | 548/240 |

OTHER PUBLICATIONS

Sokolov, S. V. et al., Chemical Abstract 55:7399 (1961) Abstracting "Isoxazole Compounds III Synthesis of Some Isoxazolylazoles", Zhur. Obshchei Khim, 30, pp. 1781–1787 (1960).
Kano, H., et al., Chem. Abstract 62:9139a (1965) Abstracting French 1,376,432 (Oct. 23, 1964).
Kano, H., et al., Chemical Abstract 63:8367a (1965) Abstracting French 1,380,177 (Nov. 27, 1964).
Takahi, Y., et al., Chemical Abstract 81:22233c (1974) Abstracting Japan Kokai 7399336 (Dec. 15, 1973).
Boyce, C. B., et al., Chemical Abstract 87:23258a (1977), Abstracting German Offen 2,639,189 (Mar. 10, 1977).
Funaki, Y., et al., Chemical Abstract 92:128915u (1980), Abstracting Japan Kokai 79 76,579 (Jun. 19, 1979).
Kelly, R. C., et al., Chemical Abstract 93:114498u (1960), Abstracting German Offen. 2,918,878 (Nov. 22, 1979).
Haken, P. T., et al., Chemical Abstract 93:132471j (1980), Abstracting Brit. Pat. Appln. 2,024,218 (Jan. 9, 1980).

*Primary Examiner*—Donald G. Daus
*Assistant Examiner*—Mark W. Noel
*Attorney, Agent, or Firm*—Seidel, Gonda, Lavorgna & Monaco

[57] ABSTRACT

This invention pertains generally to substituted 2-methylisoxazolines and more specifically to 3,5-diphenyl-3-[(1H-imidazol-1-ylmethyl) or (1H-1,2,4-triazol-1-yl-methyl)]-2-methyl-4-isoxazoline derivatives which are useful as antifungal agents.

5 Claims, No Drawings

3,5-DIPHENYL-3-[(1H-IMIDAZOL-1-YLMETHYL) OR (1H-1,2,4-TRIAZOL-1-YLMETHYL)]-2-METHYL-4-ISOXAZOLINES

BACKGROUND OF THE INVENTION

This invention pertains generally to substituted 2-methylisoxazolines and more specifically to 3,5-diphenyl-3-[(1H-imidazol-1-ylmethyl) or (1H-1,2,4-triazol-1-yl-methyl)]-2-methyl-4-isoxazoline derivatives which are useful as antifungal agents.

BRIEF SUMMARY OF THE INVENTION

In accordance with this invention there are provided compounds of the formula:

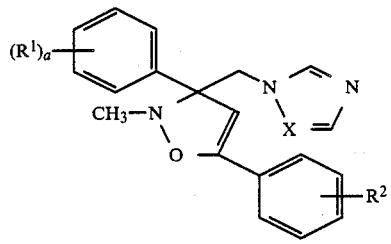

and the pharmaceutically acceptable acid addition salts thereof, in the form of their enantiomers or mixtures of their enantiomers, wherein a=1 or 2, $R^1$ is selected from hydrogen, halogen, lower alkyl, lower alkoxy and combinations thereof, provided that $R^1$ is hydrogen in the ortho position, $R^2$ is either hydrogen or represents one or more substituents selected from halogen, lower alkyl, lower alkoxy and combinations thereof, and X is CH or N.

DETAILED DESCRIPTION OF THE INVENTION

The compounds of this invention are useful as antifungal agents. They have in vitro activity against yeast and systemic mycoses and dermatophytes as determined by broth and agar testing techniques [(McGinnis, M. R., *Laboratory Handbook of Medical Mycology*, Academic Press, New York, N.Y., (1980)]. The compound prepared in Example 1 was found to have good to moderate inhibitory activity against a broad spectrum of organisms including *Trichophyton mentagrophytes, Trichophyton rubrum, Trichophyton tonsurans, Trichophyton schoenleinii, Epidermophyton floccosum, Candida stellatoidea* and *Candida albicans* with a minimum inhibitory concentration, MIC, of 0.2 to 20 ug/ml.

Because of their antifungal activity, the compounds of the invention can be used, for example, in suitable liquid, semisolid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

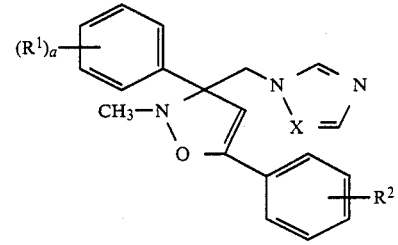

and the pharmaceutically acceptable acid addition salts thereof, in the form of their enantiomers or mixtures of their enantiomers, wherein a=1 or 2, $R^1$ is selected from hydrogen, halogen, lower alkyl, lower alkoxy and combinations thereof, provided that $R^1$ is hydrogen in the ortho position, $R^2$ is either hydrogen or represents one or more (and preferably one or two) substituents selected from halogen, lower alkyl, lower alkoxy and combinations thereof, and X is CH or N.

By halogen is meant chlorine, bromine, fluorine and iodine with chlorine and fluorine being preferred, by lower alkyl is meant groups containing one to four (1-4) carbons and by lower alkoxy is meant such groups containing one to six (1-6) carbons. In either case such groups containing three or more carbons can have a branched or unbranched chain.

The 3,5-diphenyl-3-[(1H-imidazol-1-ylmethyl) or (1H-1,2,4-triazol-1-ylmethyl)]-2-methyl-4-isoxazoline derivatives of this invention are obtained as racemic mixtures due to the presence of an asymmetric carbon atom in the isoxazoline ring. The racemic mixtures are resolvable into their optical enantiomers with (+)- and (−)-optical rotations by standard techniques such as fractional recrystallization of adducts with optically active organic acids such as (+)- and (−)-tartaric acid, (+)- and (−)-dibenzoyltartaric acid and the like.

The compounds of the invention can be prepared as illustrated in the following diagram. The synthesis of the nitrone precursor 1 is accomplished by reacting an appropriately substituted 2-imidazolylacetophenone with N-methylhydroxylamine hydrochloride as described in our copending application Ser. No. 900,856 filed Aug. 27, 1986 (now U.S. Pat. No. 4,803,282) whose disclosure is incorporated herein by reference. Subsequent reaction of nitrone 1 with the 1-alkyne derivative 2 provides a racemic mixture of the desired 3,5-diphenyl-3-(1H-imidazol-1-ylmethyl)-2-methyl-4-isoxazoline derivative 3. Similarly by using a 2-(1H-1,2,4-triazol-1-yl)acetophenone the corresponding 3-(1H-1,2,4-triazol-1-ylmethyl)isoxazoline derivatives can be prepared.

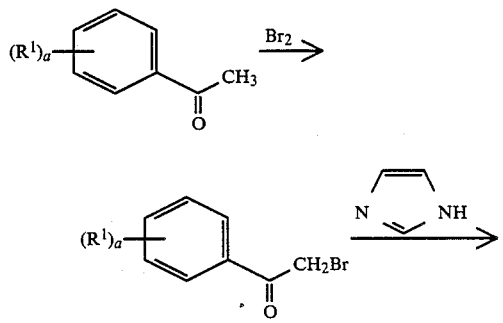

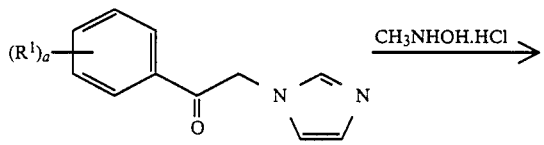

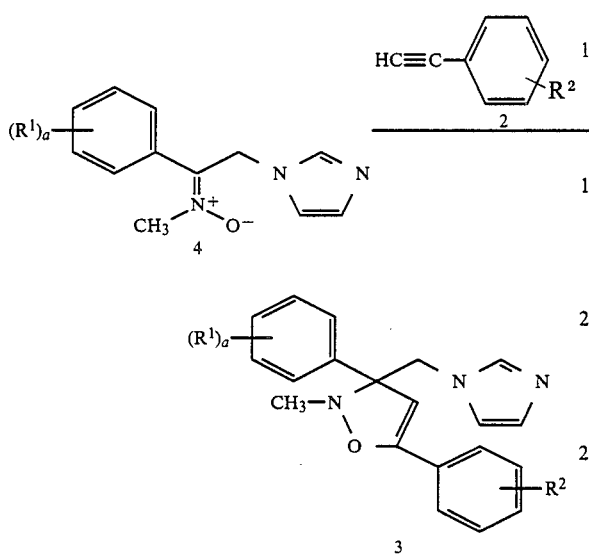

The compounds of this invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following examples.

EXAMPLE 1

3-(4-Fluorophenyl)-3-(1H-imidazol-1-ylmethyl)-2-methyl-5-phenyl-4-isoxazoline (3, $R^1$=4-F, $R^2$=H)

A solution of 2.17 g (0.0093 mol) of 1-(4-fluorophenyl)-2-(1H-imidazol-1-yl)-N-methylethanimine N-oxide (1, $R^1$=4-F) [prepared by reacting 2-(1H-imidazol-1-yl)-4'-fluoroacetophenone (17.24 g, 0.0844 mol), N-methylhydroxylamine hydrochloride (10.29 g, 0.123 mol) and sodium acetate (10.16 g, 0.124 mol) in 250 ml ethanol] and 1.50 ml (0.0136 mol) of phenylacetylene (2, $R^2$=H) in 50 ml of benzene was heated to reflux under nitrogen atmosphere and stirred for 42 hours. Upon cooling to ambient temperature, the reaction was concentrated in vacuo to a viscous oil. Addition of ethyl acetate gave 1.42 g (45.5%) of compound 3 ($R^1$=4-F, $R^2$=H) as white needles, m.p. 149°–150° C. (ethyl acetate). Anal. Calcd. for $C_{20}H_{18}FN_3O$: C, 71,63; H, 5.41; F, 5.66; N, 12.53. Found: C, 71.76; H, 5.42; F, 5.66; N, 12.45.

EXAMPLE 2

3-(4-Chlorophenyl)-3-(1H-imidazol-1-ylmethyl)-2-methyl-5-phenyl-4-isoxazoline (3, $R^1$=4-Cl, $R^2$=H)

Compound 3 ($R^1$=4-Cl, $R^2$=H) was prepared by a method similar to that described in Example 1 from 8.50 g (0.041 mol) of 1-(4-chlorophenyl)-2-(1H-imidazol-1-yl)-N-methylethanimine N-oxide (1, $R^1$=4-Cl) and 6.68 ml (0.061 mol) of phenylacetylene (2, $R^2$=H). Crystallization from ether gave 4.00 g (27.7%) of compound 3 ($R^1$=4-Cl, $R^2$=H), m.p. 171°–174° C. (ethyl acetate). Anal. Calcd. for $C_{20}H_{18}ClN_3O$: C, 68.28; H, 5.16; N, 11.94. Found: C, 68.20; H, 5.22; N, 11.92.

EXAMPLE 3

3-(Phenyl or substituted phenyl)-3-(1H-1,2,4-triazol-1-yl-methyl)-2-methyl-5-(phenyl or substituted phenyl)-4-isoxazolines By following essentially the same methods as described for Examples 1 and 2 and substituting a 1-(phenyl or substituted phenyl)-2-(1H-1,2,4-triazol-1-yl)-N-methylethanimine N-oxide for 1-(4-fluoro or 4-chlorophenyl)-2-(1H-imidazol-1-yl)-N-methylethamine N-oxide, the corresponding triazolyl derivatives can be prepared.

For example,
3-(4-fluorophenyl)-3-(1H-1,2,4-triazol-1-ylmethyl)-2-methyl-5-phenyl-4-isoxazoline,
3-(4-chlorophenyl)-3-(1H-1,2,4-triazol-1-ylmethyl)-2-methyl-5-phenyl-4-isoxazoline,
3-(4-methoxyphenyl)-3-(1H-1,2,4-triazol-1-ylmethyl)-2-methyl-5-(4-chlorophenyl)-4-isoxazoline, or
3-(3-methylphenyl)-3-(1H-1,2,4-triazol-1-ylmethyl)-2-methyl-5-(4-methoxyphenyl)-4-isoxazoline.

EXAMPLE 4

3-(Phenyl or substituted phenyl)-3-(1H-imidazol)-1-ylmethyl)-2-methyl-5-(phenyl or substituted phenyl)-4-isoxazolines By following essentially the same methods as described in Example 1 and replacing 1-(4-fluorophenyl)-2-(1H-imidazol-1-yl)-N-methylethanimine N-oxide by 1-phenyl-2-(1H-imidazol-1-yl)-N-methylethanimine N-oxide, or 1-(4-methylphenyl)-2-(1H-imidazol-1-yl)-N-methylethanimine N-oxide, or 1-(4-chloro-3-methylphenyl)-2-(1H-imidazol-1-yl)-N-methylethanimine N-oxide, and replacing phenylacetylene by,
1-(4-chlorophenyl)acetylene, or
1-(3-methylphenyl)acetylene, or
1-(4-methoxyphenyl)acetylene
the corresponding 4-isoxazoline derivatives can be prepared.

For example,
3-phenyl-3-(1H-imidazol-1-ylmethyl)-2-methyl-5-(4-chlorophenyl)-4-isoxazoline,
3-(4-methoxyphenyl)-3-(1H-imidazol-1-ylmethyl)-2-methyl-5-(3-methylphenyl)-4-isoxazoline,
3-(4-methylphenyl)-3-(1H-imidazol-1-ylmethyl)-2-methyl-5-(4-methoxyphenyl)-4-isoxazoline, and
3-(4-chloro-3-methylphenyl)-3-(1H-imidazol-1-ylmethyl)-2-methyl-5-(4-chlorophenyl)isoxazoline.

We claim:
1. A compound of the formula:

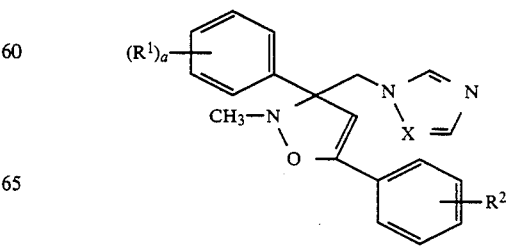

and the pharmaceutically acceptable acid addition salts thereof, in the form of their enantiomers or mixtures of their enantiomers, wherein a=1 or 2, $R^1$ is selected from hydrogen, halogen, lower alkyl, lower alkoxy and combinations thereof, provided that $R^1$ is hydrogen in the ortho position, $R^2$ is either hydrogen or represents one or two substituents selected from halogen, lower alkyl, lower alkoxy and combinations thereof, and X is CH or N.

2. The compound of claim 1 wherein X=CH.
3. The compound of claim 1 wherein X=N.
4. The compound of claim 1 wherein the compound is 3-(4-fluorophenyl)-3-(1H-imidazol-1-ylmethyl)-2-methyl-5-phenyl-4-isoxazoline.
5. The compound of claim 1 wherein the compound is 3-(4-chlorophenyl)-3-(1H-imidazol-1-ylmethyl)-2-methyl-5-phenyl-4-isoxazoline.

* * * * *